(12) United States Patent
Berry

(10) Patent No.: US 12,048,632 B2
(45) Date of Patent: Jul. 30, 2024

(54) EXPANDABLE INTERBODY IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 734 days.

(21) Appl. No.: 17/223,532

(22) Filed: Apr. 6, 2021

(65) Prior Publication Data

US 2021/0220147 A1    Jul. 22, 2021

Related U.S. Application Data

(63) Continuation-in-part of application No. 17/140,761, filed on Jan. 4, 2021, now Pat. No. 11,793,651, and a continuation-in-part of application No. 16/600,134, filed on Oct. 11, 2019, now Pat. No. 11,304,821, which is a continuation-in-part of application No. 16/409,149, filed on May 10, 2019, now Pat. No. 10,881,531.

(51) Int. Cl.
*A61F 2/44*    (2006.01)
*A61F 2/30*    (2006.01)

(52) U.S. Cl.
CPC .. *A61F 2/4425* (2013.01); *A61F 2002/30281* (2013.01); *A61F 2002/30405* (2013.01); *A61F 2002/443* (2013.01)

(58) Field of Classification Search
CPC ............ A61F 2002/30579; A61F 2/447; A61F 2/4455
See application file for complete search history.

(56) References Cited

U.S. PATENT DOCUMENTS

| | | | |
|---|---|---|---|
| 10,022,239 B1 * | 7/2018 | Lentner | A61F 2/447 |
| 10,098,759 B2 | 10/2018 | Weiman | |
| 10,441,430 B2 | 10/2019 | Ludwig et al. | |
| 11,304,821 B2 * | 4/2022 | Berry | A61F 2/447 |
| 2011/0093074 A1 * | 4/2011 | Glerum | A61F 2/447 623/17.16 |
| 2014/0039622 A1 * | 2/2014 | Glerum | A61F 2/447 623/17.15 |

(Continued)

FOREIGN PATENT DOCUMENTS

DE    102018206693 B3    2/2019

OTHER PUBLICATIONS

International Search Report and Written Opinion for PCT Patent Application No. PCT/US20/55042, mailed Jan. 21, 2021.

*Primary Examiner* — Eduardo C Robert
*Assistant Examiner* — Michelle C Eckman
(74) *Attorney, Agent, or Firm* — McCarter & English, LLP; James M. Smedley; Alex Korona

(57) ABSTRACT

The present invention generally relates to an expandable interbody implant. Specifically, the present invention is an expandable interbody implant having an anterior and posterior wedge and opposing endplates. In some embodiments, a slot parallel to the wedge face may be located on each endplate, with a pin holding the endplates to the respective wedges. Additionally, in some implementations, lateral rails may extend from the anterior wedge to the posterior wedge. Furthermore, the expandable implant may include a locking mechanism configured to prevent unwanted collapse.

17 Claims, 6 Drawing Sheets

(56) References Cited

U.S. PATENT DOCUMENTS

| | | | |
|---|---|---|---|
| 2014/0257484 A1* | 9/2014 | Flower | A61F 2/4455 29/460 |
| 2017/0224504 A1* | 8/2017 | Butler | A61F 2/447 |
| 2018/0193164 A1* | 7/2018 | Shoshtaev | A61F 2/4425 |
| 2019/0269521 A1* | 9/2019 | Shoshtaev | A61F 2/4455 |
| 2019/0388232 A1 | 12/2019 | Purcell et al. | |
| 2020/0352731 A1 | 11/2020 | Berry | |

* cited by examiner

EXPANDABLE INTERBODY IMPLANT

CROSS-REFERENCE TO RELATED APPLICATIONS

This application is a continuation-in-part of U.S. application Ser. No. 16/600,134, entitled "Dual Expandable Spinal Implant", filed on Oct. 11, 2019 which is a continuation-in-part of U.S. application Ser. No. 16/409,149, entitled "Dual Expandable Spinal Implant", filed on May 10, 2019, now U.S. Pat. No. 10,881,531, issued on Jan. 5, 2021, and a continuation-in-part of U.S. application Ser. No. 17/140,761, entitled "Expandable Implant", filed on Jan. 4, 2021, the entire disclosures of which are incorporated herein by reference.

TECHNICAL FIELD

Various embodiments relate generally to expandable interbody implants.

BACKGROUND

Expandable interbody implants are commonly used to treat a variety of spinal problems. Such implants may generally be configured to improve sagittal alignment.

Expandable interbody implants having opposing wedges are advantageous to patients and surgeons, as they are relatively simple devices having few moving parts. However, the drawbacks of the expandable interbody implant devices presently known in the art are their use of multiple angled grooves and rails, or angled dovetails which are not effective in preventing the devices from over-expanding, or their need to be comprised from a plurality of components, requiring each component to be smaller, and thus, effectively weaker. For example, the device disclosed in U.S. Pat. No. 10,098,759 uses multiple angled grooves and rails, or angled dovetails to prevent its endplates from falling off. However, such angled components do not prevent the implant's endplates from over-extending or the implant itself from over-expanding and/or disassembling. Furthermore, such a configuration is difficult to manufacture, as all the grooves, rails, and/or dovetails must be properly aligned. Additionally, in some cases, rotation of the implant's expansion screw often causes the rotation of such devices' anterior wedge causing such devices to rely on exterior pressure or on certain portions of the endplates to prevent such rotation of the anterior wedge. However, relying on exterior pressure can lead the implant to bind, as the implant components try to twist against each other, thereby increasing the force needed to expand the device. Some devices, such as U.S. Pat. No. 10,441,430, which are relatively small but are made of numerous components, compromise the integrity of the device as the smaller the pieces, the weaker the overall device. Moreover, these prior devices lack an adequate locking mechanism for locking the device in its expanded position. Without such a locking mechanism, the devices are susceptible to collapse under the constant load of the spine. In some scenarios, the devices in the prior art have been recalled for just such issues.

The present disclosure is directed at a device having the ability to expand in at least one plane, while maintaining alignment of the device's endplates, and preventing a first wedge component from rotating with respect to a second wedge component. These and other features and advantages of the present invention will become obvious to one skilled in the art through the summary of the invention that follows.

SUMMARY

Apparatus and associated methods relate to an expandable interbody implant configured to expand in at least one plane when a threaded post disposed between a pair of opposing wedges directs the wedges closer together as the threaded post is rotated to drive movable endplates operably engaged with the wedges radially outward from a longitudinal axis of the threaded post. In an illustrative example, the wedges may be a pair of wedges configured with dual inclined faces. Some embodiments may include an aligning support. In some examples, the aligning support comprises one or more rails adapted to engage with and prevent rotation of the wedges. In some embodiments, the endplates include one or more elongated slots running parallel to the angled faces of the endplates. One or more connectors may run through the elongated connector slots and into each wedge, to secure the endplates to the wedges. These connectors, for example, pins, may allow the endplates to move along the wedge faces, but may also prevent the endplates from over-extending or disassembling. Moreover, a threaded post may be rotated to engage and pull a first wedge (e.g. an anterior wedge) towards a second wedge (e.g. a posterior wedge). This action may direct the endplates, for example, superior and inferior endplates, to expand superiorly and inferiorly. Moreover, a locking mechanism, for example, a set screw may be threaded into a posterior portion of the second wedge (e.g. the posterior wedge) and against the threaded post, which may prevent the threaded post from counter-rotating. This may maintain the expanded height of the device and may avert unwanted collapse.

The details of various embodiments are set forth in the accompanying drawings and the description below. Other features and advantages will be apparent from the description and drawings, and from the claims.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED DESCRIPTION OF ILLUSTRATIVE EMBODIMENTS

Figure 1:
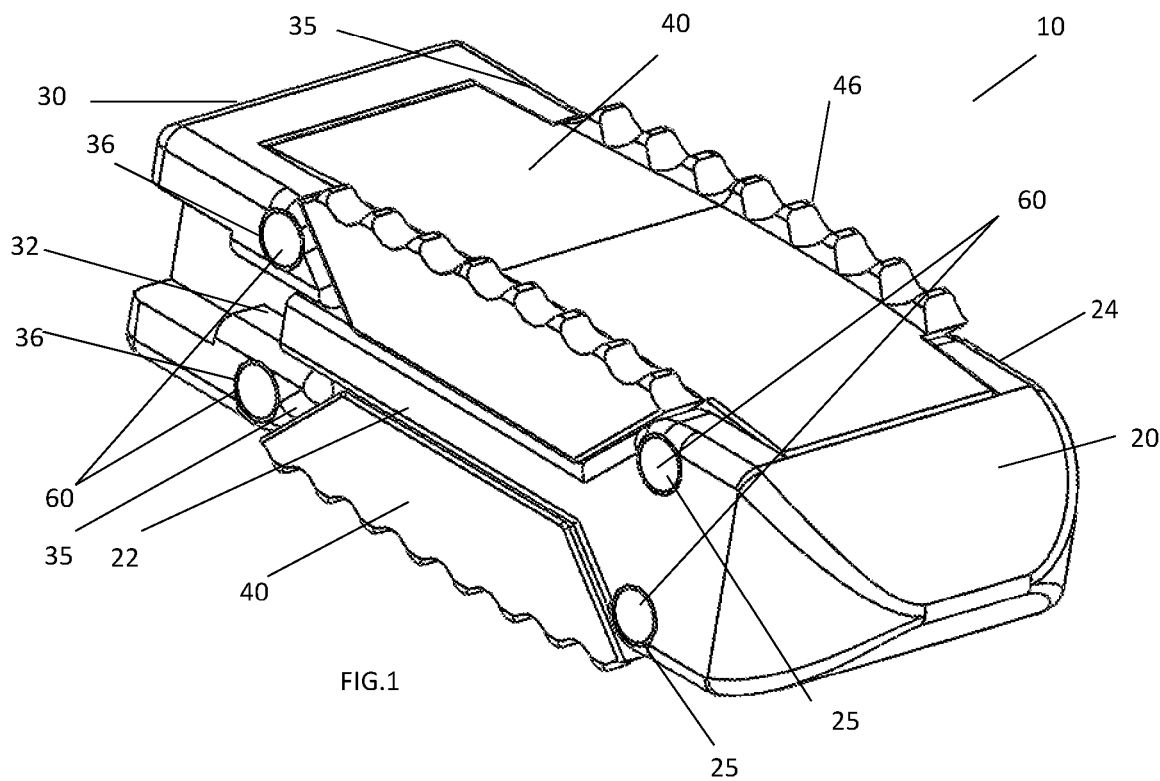
FIG. 1 depicts a top, front perspective view of an embodiment interbody implant in an illustrative unexpanded configuration.

FIGS. 1-11 demonstrate exemplary embodiments that illustrate the design and operation of exemplary expandable interbody implant implementations. Specifically, various views of an exemplary expandable interbody implant depicted in illustrative configurations are disclosed, to explain improvements in expandable interbody implant design.

In general, FIGS. 1-11 depict an implant 10 having a pair of opposing wedges, for example, an anterior wedge 20 and a posterior wedge 30 disposed between a pair of endplates 40, operably connected by a threaded post 50, and aligned by an aligning support, for example, a pair of rails 22. In some examples, the anterior wedge 20 comprises one or more interior faces 21, one or more rails 22, an internal hole 23 having a threaded portion 26, one or more guide tracks 24, and one or more connector holes 25 and the posterior wedge 30 comprises one or more interior faces 31, one or more lateral grooves 32, an internal hole 33 having a threaded portion 34, one or more guide tabs 35, one or more connectors holes 36, and one or more inserter indentations 37. In some scenarios, the endplates 40 comprise one or more anterior faces 41, one or more posterior faces 42, one or more connector slots 43, one or more anterior guide grooves 44, one or more posterior guide grooves 45, and a plurality of ridges 46. In some embodiments, the threaded post 50 comprises a posterior cylinder 51, a threaded tip 52, a drive feature 53, and a retention groove 54. In some examples, one or more implant components may be operably connected by one or more connectors 60. In some embodiments, the implant may further comprise a locking mechanism, for example, a locking screw 70 having an external threaded portion 71 and a drive feature 72.

FIG. 1 depicts a top, rear perspective view of an embodiment interbody implant in an illustrative unexpanded configuration. In FIG. 1, the exemplary unexpanded implant 10 includes a posterior wedge 30 axially coupled with an anterior wedge 20 by a threaded post 50. In some embodiments, the implant 10 may further comprise two or more opposing endplates 40, for example, parallel opposing endplates. In the illustrated example, the implant 10 comprises two parallel endplates 40, one on a superior side of the implant 10 and one on the inferior side of the implant 10. In the depicted example, the endplates 40 include ridges or teeth 46 configured to bite into vertebral endplates and secure the implant 10 to a spine. In some examples, the anterior wedge 20 includes an aligning support. In the illustrated embodiment, the aligning support comprises one or more rails 22 which laterally extend from the anterior wedge 20 towards the posterior wedge 30 and are configured to engage with lateral grooves 32 (also referred to herein as posterior wedge rail inserts) in the posterior wedge 30. In some embodiments, connectors 60 may be utilized to operably connect the wedges 20 and 30 to the endplates 40. In some embodiments, the connectors 60 may be or may comprise pins, screws, clips, clasps or other similar connecting members suitable to similarly operably connect the endplates 40 to the anterior and posterior wedges 20 and 30. Further in the depicted example, extending anteriorly from the posterior wedge 30 are guide tabs 35. In the illustrated embodiment, connector holes 36 are disposed on the guide tabs 35. In the depicted example, extending posteriorly from the anterior wedge 20 are guide tracks 24. In the illustrated example, connector holes 25 are disposed on the guide tracks 24, which run along a lateral axis. In some embodiments, the endplates 40 may be configured to rest or slide against at least one face of either or both of the guide tabs 35 and the guide tracks 24. In the illustrated example, the connectors 60 are in a first position in the connector slots (not shown) of the endplates 40 when the implant 10 is in the unexpanded position.

Figure 2:
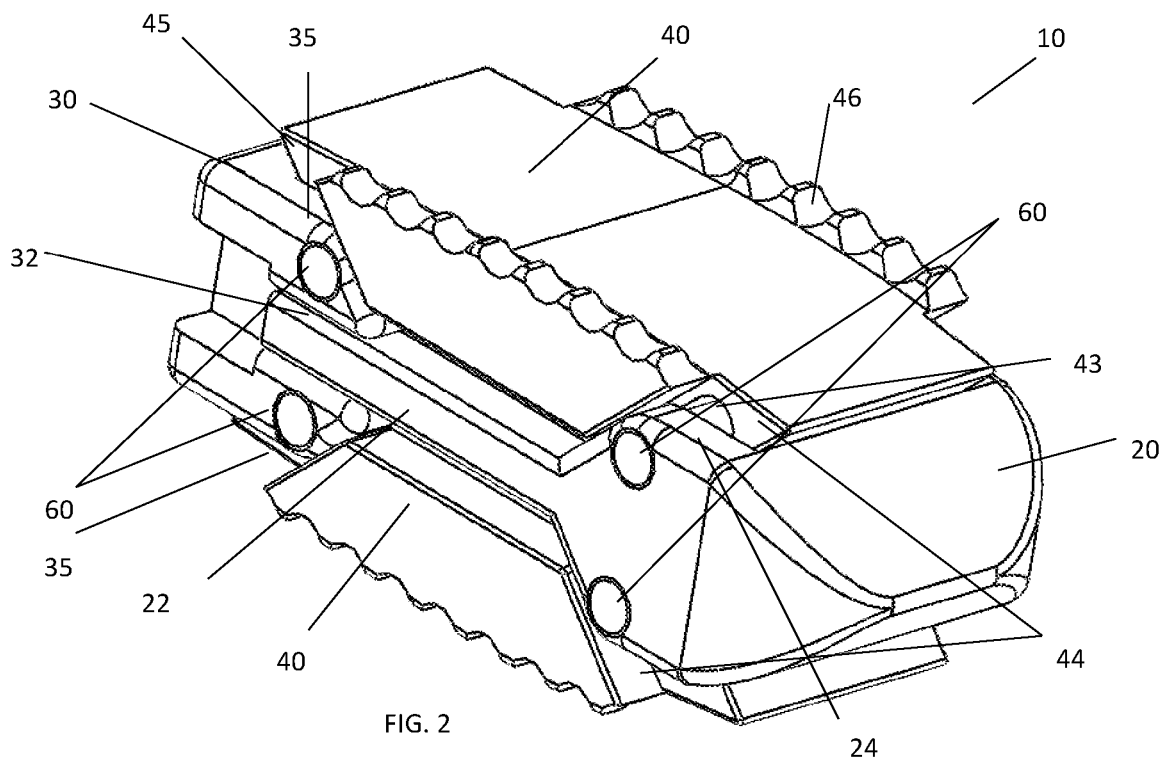
FIG. 2 depicts a top, rear perspective view of an embodiment interbody implant in an illustrative expanded configuration.

FIG. 2 depicts a top, rear perspective view of an embodiment interbody implant in an illustrative unexpanded configuration. In FIG. 2, endplates 40 are disposed between the anterior wedge 20 and the posterior wedge 30, one on the inferior side, and one on the superior side. In the depicted example, the threaded post (not shown) is engaged with the anterior and posterior wedges 20 and 30, respectively, and has directed the two wedges 20 and 30 towards each other such that the interior faces 21 and 31 of the wedges 20 and 30, respectively, engage with anterior and posterior internal faces 41 and 42, respectively, of the endplates 40 to expand the implant 10, for example, to expand the height of the implant 10. As shown in the depicted example, extending from the anterior wedge 20 are one or more rails 22 which may be configured to slidably engage with the posterior wedge rail inserts 32 to maintain the alignment of the anterior and posterior wedges 20 and 30. In the illustrated example, the connectors 60 are in a second position in the connector slots 43 of the endplates 40 when the implant 10 is in the expanded position.

Figure 3:
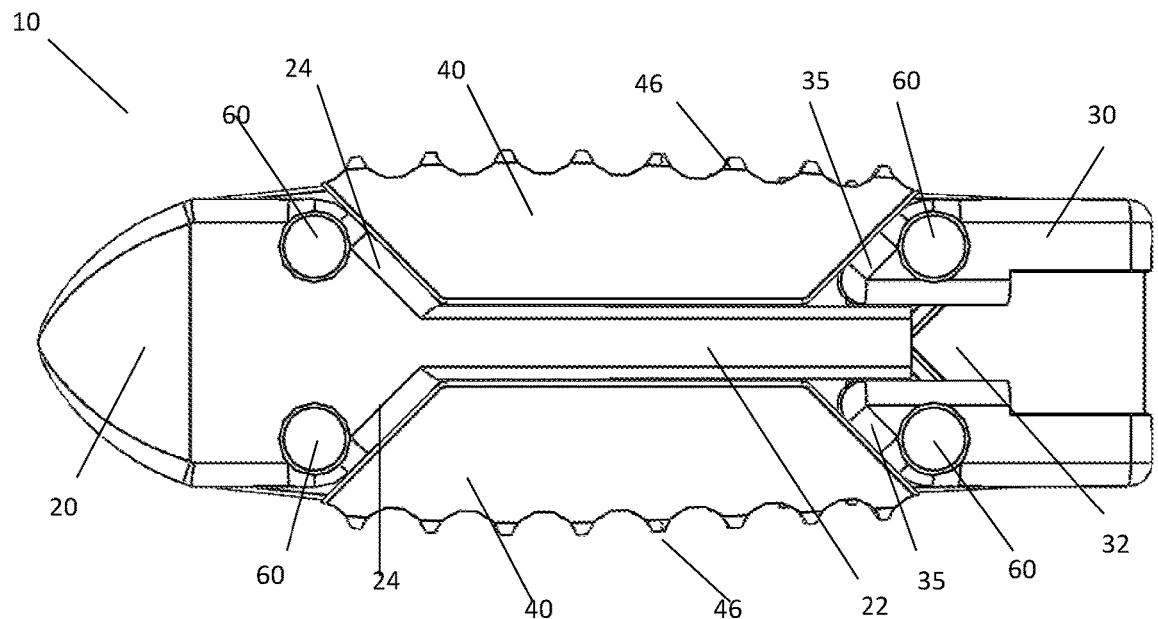
FIG. 3 depicts a side view of an embodiment interbody implant in an illustrative unexpanded configuration.
Figure 11:
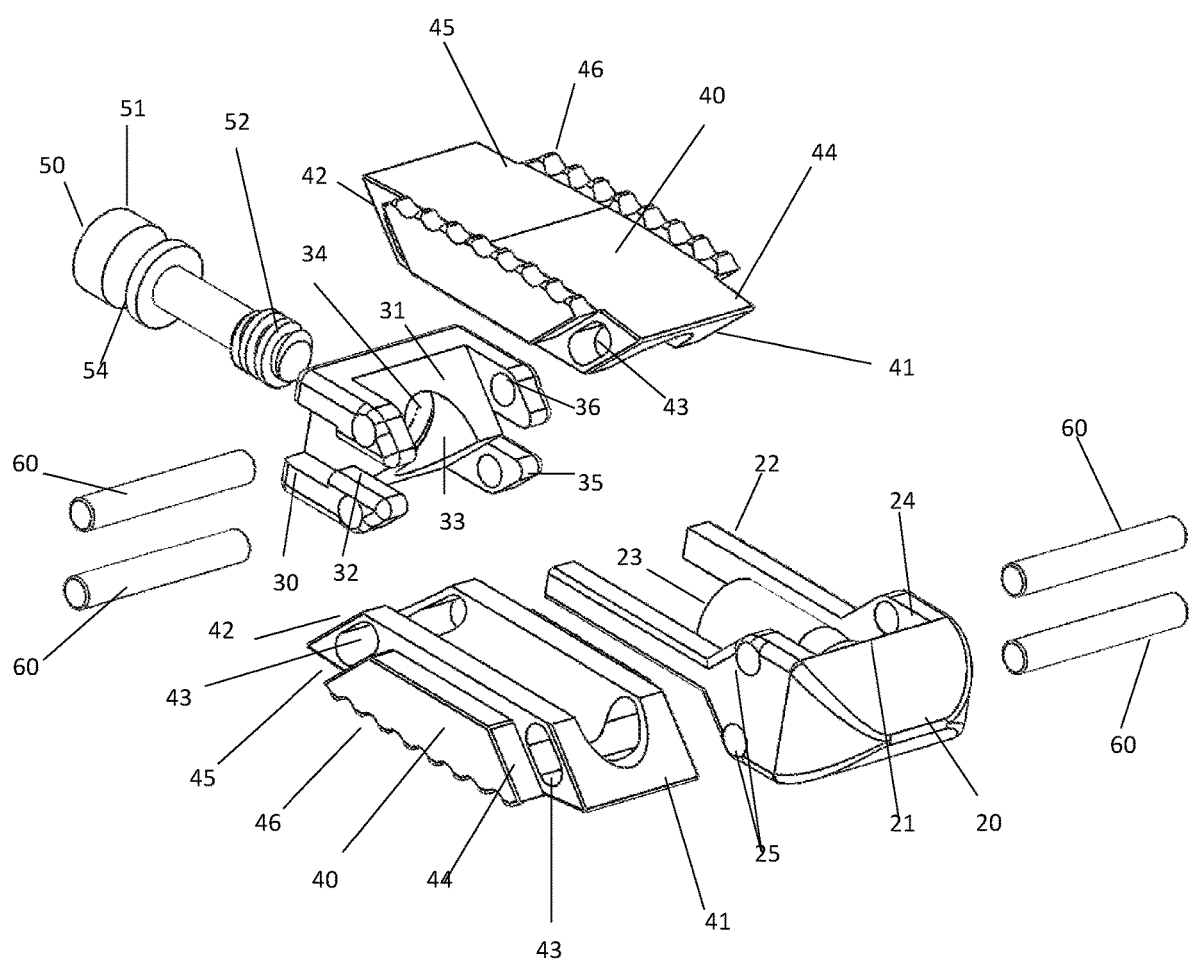
FIG. 11 depicts an exploded view of an embodiment interbody implant.

FIG. 3 depicts a side view of an embodiment interbody implant in an illustrative unexpanded configuration. In FIG. 3, rails 22 are shown which extend posteriorly from the anterior wedge 20 and into a pair of lateral grooves 32 (as best shown in FIG. 11) on the posterior wedge 30. In some scenarios, this configuration substantially aligns the anterior and posterior wedges 20 and 30 and allows the anterior wedge 20 to translate anterior-posteriorly with respect to the posterior wedge 30 while minimizing or altogether restricting any rotation, lateral, or inferior-superior motion. In some examples, the rails 22 may be rods, protruding guides or tracks capable of aligning the anterior and posterior wedges 20 and 30 in a similarly suitable manner. In the illustrated example, at least one face of each guide tab 35 rests against or is substantially aligned with an inclined face of the endplates 40. Similarly, as shown in the depicted example, at least one face of each guide track 24 rests against or is substantially aligned with an inclined face of the endplates.

Figure 4:
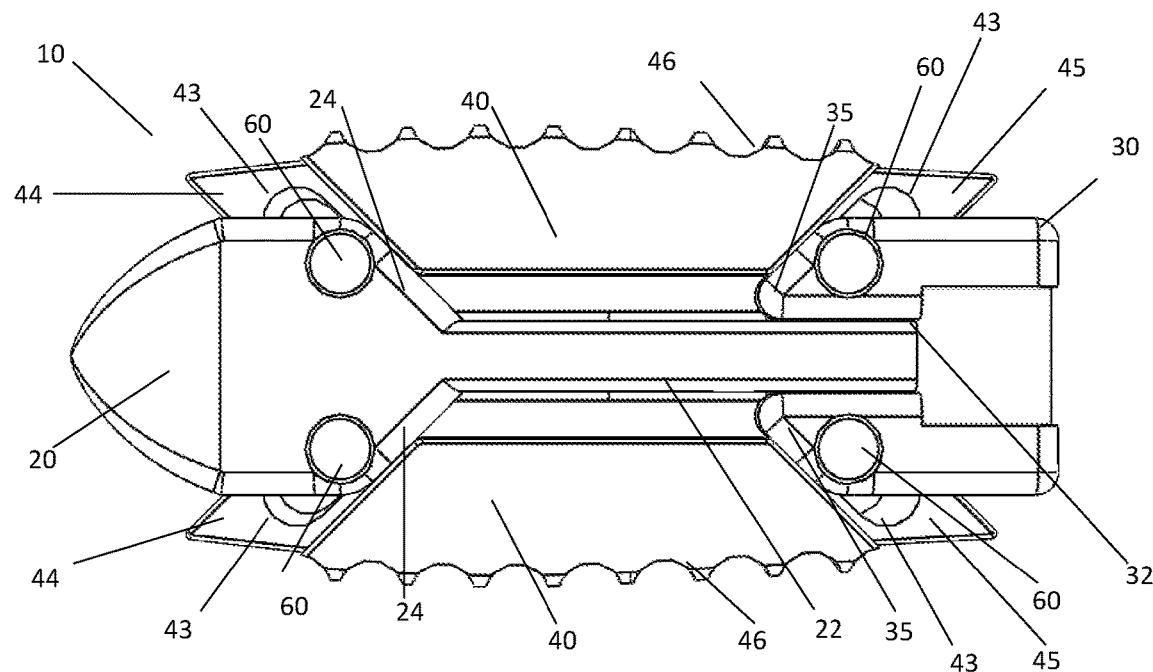
FIG. 4 depicts a side view of an embodiment interbody implant in an illustrative expanded configuration.

FIG. 4 depicts a side view of an embodiment interbody implant in an illustrative expanded configuration. In FIG. 4, an expanded implant configuration is shown, wherein the movement of the anterior wedge 20 towards the posterior wedge 30, directed the two endplates 40 away from one another, thereby expanding (e.g. increasing the height of) the implant 10. In the depicted example, at least one inclined face of the endplates 40 rests against or is substantially aligned with at least one face of each guide tab 35. Similarly, as shown in the depicted example, at least one inclined face of the endplates 40 rests against or is substantially aligned with at least one face of each guide track 24. In some scenarios, when the endplates 40 move to a second, or expanded position, such as the expanded position shown in FIG. 4, one or more anterior inclined faces of the endplates 40 may ride against or along the guide tracks 24 of the anterior wedge 20, in some cases, to prevent lateral movement of the endplates 40 with respect to the anterior wedge 20. Similarly, one or more posterior inclined faces of the endplates 40 may be configured to ride against or along the guide tabs 35 of the posterior wedge 30, in some cases, to prevent the lateral movement of the endplates 40 with respect to the posterior wedge 30.

Figure 5:
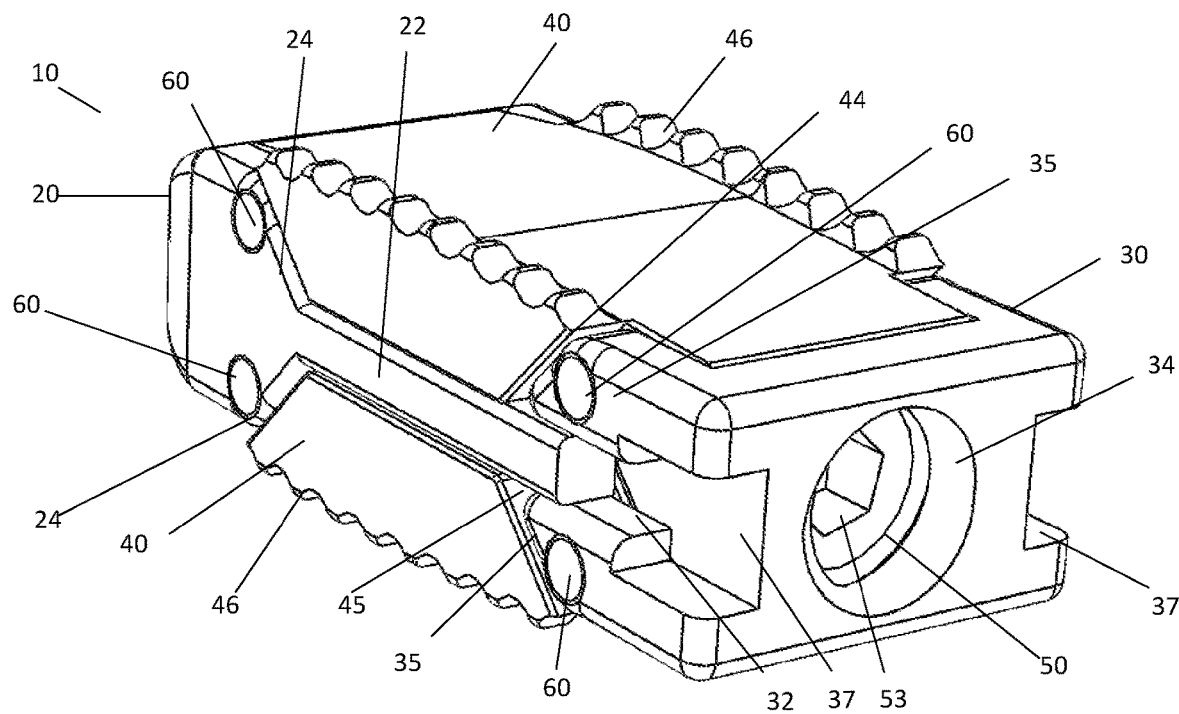
FIG. 5 depicts a top, rear perspective view of an embodiment interbody implant in an illustrative unexpanded configuration.

FIG. 5 depicts a top, rear perspective view of an embodiment interbody implant in an illustrative unexpanded configuration. In FIG. 5, the depicted rear view of the exemplary unexpanded implant 10 includes a posterior wedge 30 engaged with a threaded post 50 having a drive feature 53. In some examples, an inserter or driver (not shown) may engage with the drive feature 53 to rotate the threaded post 50.

Figure 6:
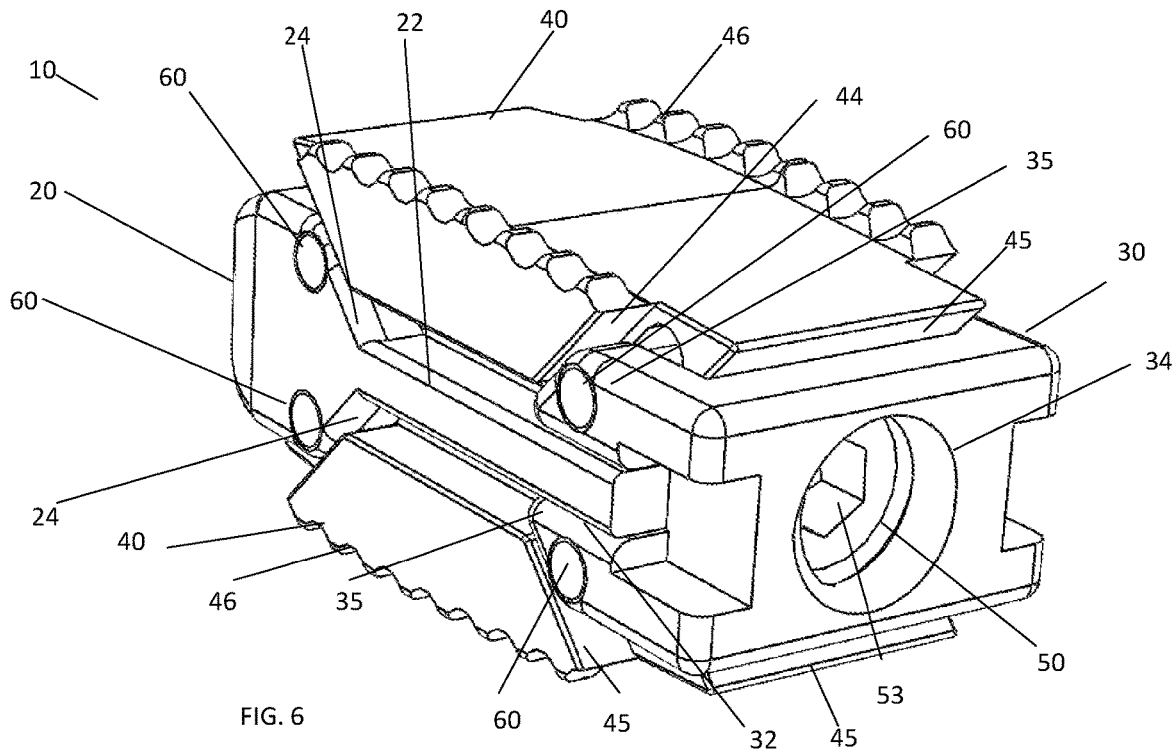
FIG. 6 depicts a top, rear perspective view of an embodiment interbody implant in an illustrative expanded configuration.

FIG. 6 depicts a top, rear perspective view of an embodiment interbody implant in an illustrative expanded configuration. In FIG. 6, the depicted rear view of the exemplary expanded implant 10 includes a posterior wedge 30 engaged with a threaded post 50 having a drive feature 53. In some examples, the posterior wedge 30 includes indentations 37 on its lateral edges to allow for an inserter (not shown) to hold and/or insert the implant 10 into a patient body. In the depicted example, the device 10 is in a second position, wherein the inferior and superior endplates 40 are radially displaced from the threaded post 50 longitudinal axis as a result of the anterior wedge 20 moving toward the posterior wedge 30, as the threaded post 50 was rotated.

Figure 7:
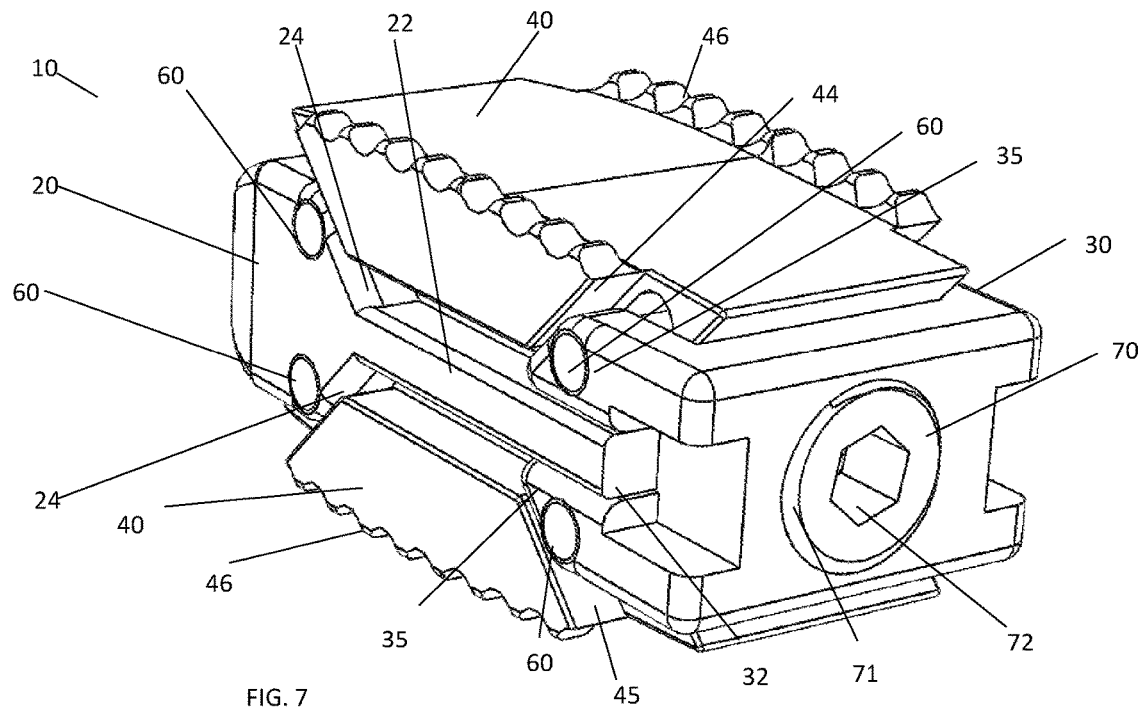
FIG. 7 depicts a top, rear perspective view of an embodiment interbody implant in an illustrative expanded configuration locked with a locking screw.

FIG. 7 depicts a top, rear perspective view of an embodiment interbody implant in an illustrative expanded configuration locked with a locking screw. In FIG. 7, a locking screw 70 is engaged with internal threads in the posterior wedge 30. As shown in the depicted example, the locking screw 70 may have an external threaded portion 71 and a drive feature 72. As shown in the illustrated embodiment, the locking screw 70 may be screwed up against and substantially abut the posterior side of the threaded post 50 to prevent the threaded post 50 from turning, thereby locking the implant 10 in the expanded position. In some embodiments, this configuration prevents the implant 10 from collapsing. In any embodiment, the locking screw 70 may be any similarly suitable locking member capable of locking the threaded post 50 in place when the implant 10 is in the expanded position.

Figure 8:
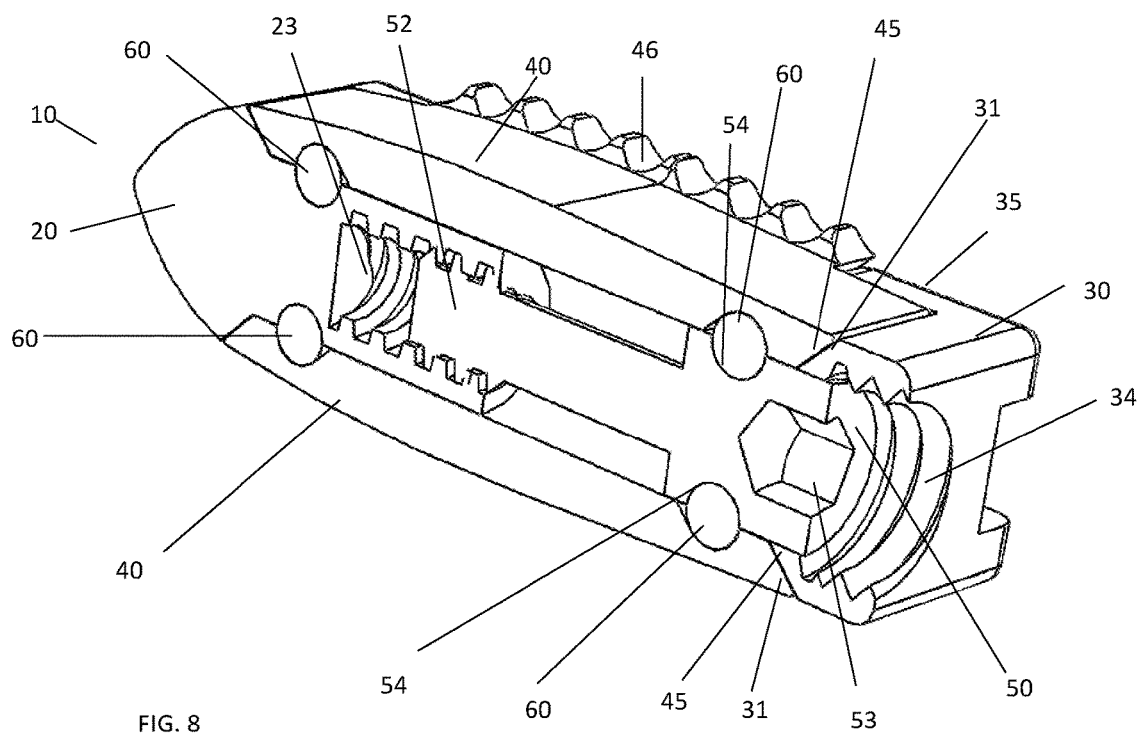
FIG. 8 depicts a cross-sectional perspective view of an embodiment interbody implant in an illustrative unexpanded configuration.

FIG. 8 depicts a cross-sectional perspective view of an embodiment interbody implant in an illustrative unexpanded configuration. In FIG. 8, a threaded post 50 runs posterior to anterior through an internal hole 33 in the posterior wedge 30 and extends to the internal hole 23 of the anterior wedge 20. As shown in FIGS. 8 and 11, the threaded post 50 may include a posterior cylinder 51 which may rest within the internal hole 33 of the posterior wedge and may be configured to spin freely within the internal hole 33 of the posterior wedge 30. In the depicted example, an anterior portion of the threaded post 50 is formed with a threaded tip 52. The threaded tip 52 of the threaded post 50 may be configured to mate with at least a portion of the threaded portion 26 of the internal hole 23 in the anterior wedge 20. In some examples, as shown in the illustrated embodiment, a posterior face of the threaded post 50 may include a drive feature 53. In some scenarios, the drive feature 53 may allow a user to rotate the threaded post 50 using an inserter or driver (not shown). In the illustrated example, the threaded post 50 further comprises a retention groove 54. In some embodiments, when the threaded post 50 is rotated, it directs the anterior wedge 20 to translate posteriorly, or anteriorly depending on the desired application of the implant 10. For example, as the threaded post 50 is turned, the anterior wedge 20 may move toward the posterior wedge 30.

Figure 9:
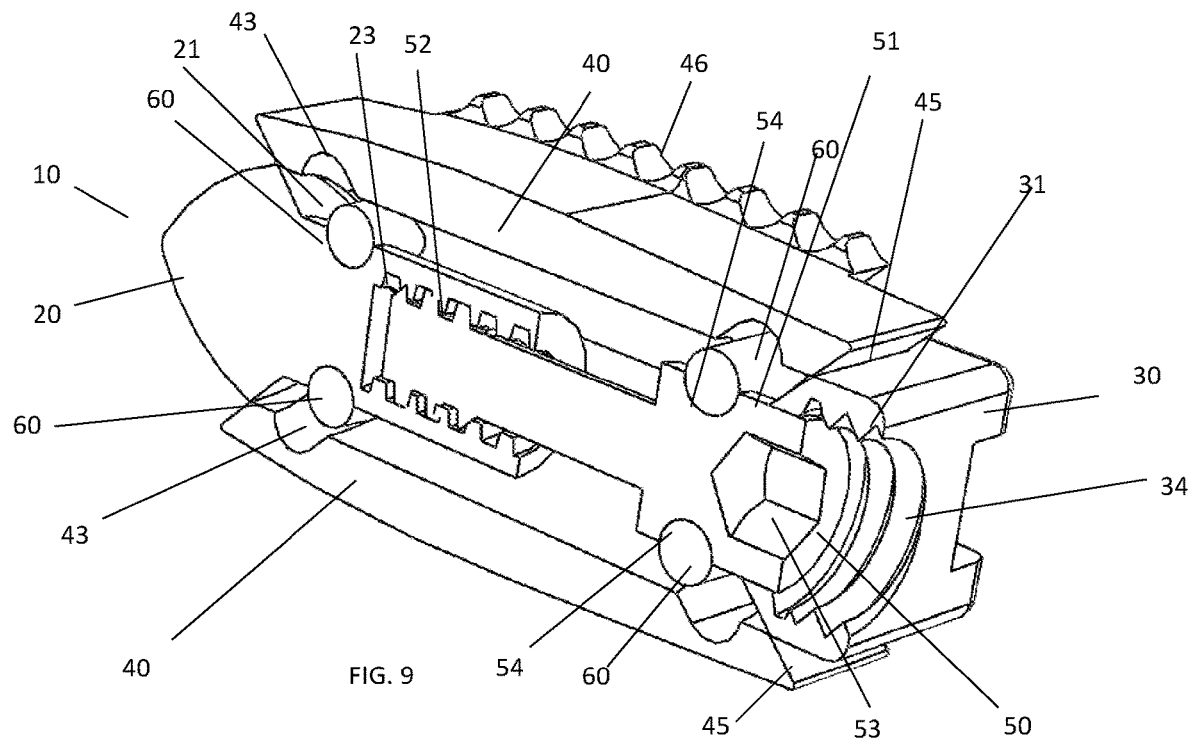
FIG. 9 depicts a cross-sectional perspective view of an embodiment interbody implant in an illustrative expanded configuration.

FIG. 9 depicts a cross-sectional perspective view of an embodiment interbody implant in an illustrative expanded configuration. In FIG. 9, connectors 60 are shown which operably connect the anterior and posterior wedges 20 and 30, respectively, to the endplates 40. In the depicted example, a first set of connectors 60 extend through connector holes 25 of the anterior wedge 20 and the anterior connector slot 43 of each endplate 40. Similarly, a second set of connectors 60 extend through the connector holes 36 of the posterior wedge 30 and the posterior connector slot 43 of each endplate 40. In some scenarios, the connectors 60 may be configured to prevent the endplates 40 from extending too far from the threaded post 50, in turn preventing the disassembly of the implant 10. In some examples, as in the example depicted in FIG. 9, the connectors 60 which extend through the connector holes 36 of the posterior wedge 30, also pass through the retention groove 54 formed in the threaded post 50. Such connectors 60 may be configured to prevent the threaded post 50 from inadvertently translating or moving within the posterior wedge 30.

Figure 10:
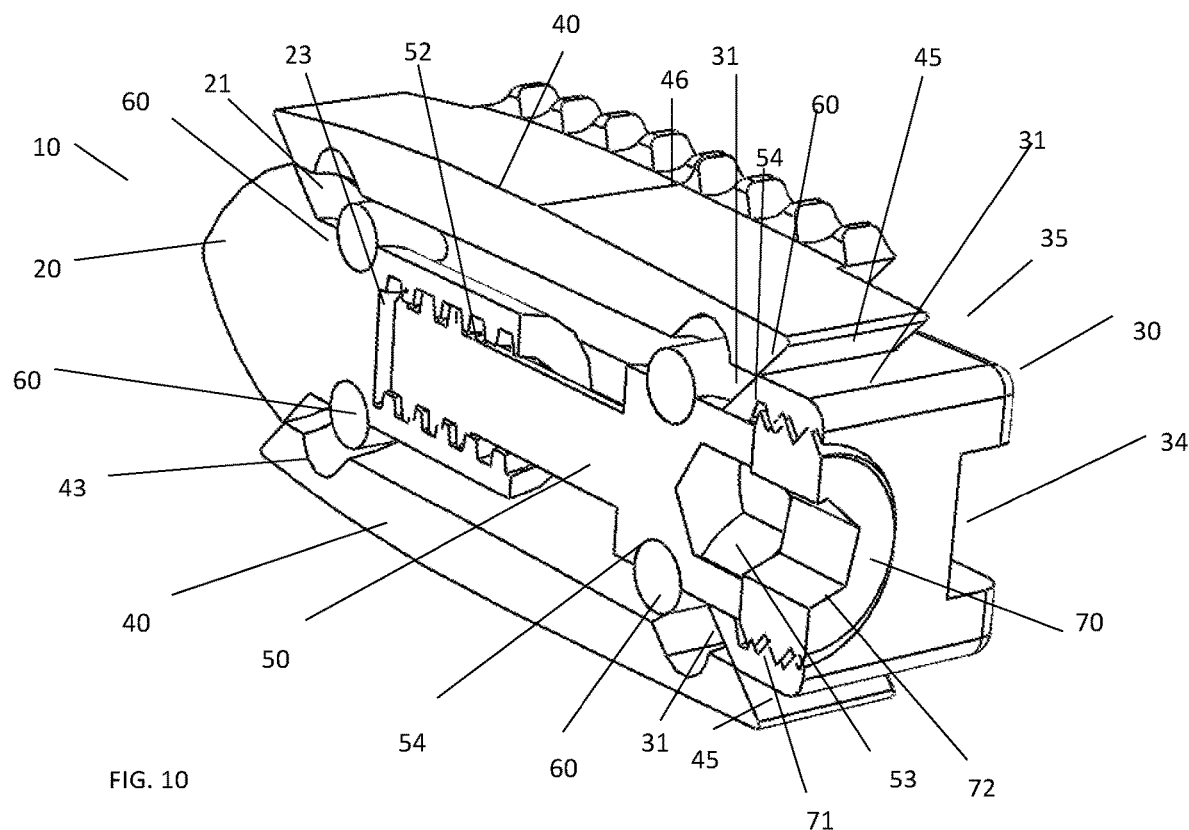
FIG. 10 depicts a cross-sectional perspective view of an embodiment interbody implant in an illustrative expanded configuration locked with a locking screw.

FIG. 10 depicts a cross-sectional perspective view of an embodiment interbody implant in an illustrative expanded configuration locked with a locking screw. As shown in the depicted example, in some scenarios, the locking screw 70 may be configured to substantially abut the threaded post 50, to substantially lock the threaded post 50 in a desired location (e.g. at a desired expansion position of the implant 10) and prevent the threaded post 70 from unscrewing or dislodging. In some scenarios, the locking screw 50 may be configured to maintain or lock the implant 10 in the expanded position.

FIG. 11 depicts an exploded view of an embodiment interbody implant. In FIG. 11, the exemplary expanded implant 10 includes an anterior wedge 20 comprising a pair of interior faces 21 and a posterior wedge 30 comprising a pair of interior faces 31. As is demonstrated in FIG. 11, the interior faces 21 and 31 of each wedge 20 and 30, respectively, may be angled. For example, the interior faces 21 of the anterior wedge 20 may be perpendicular to one another and the interior faces 31 of the posterior wedge may be perpendicular to one another. However, in some embodiments, the interior faces 21 and 31 may be angled in any appropriate orientation to create the anterior and posterior wedges 20 and 30, respectively. In the depicted example, the interior faces 21 are approximately 45 degrees from the horizontal plane, facing posteriorly and the interior faces 31 are approximately 45 degrees from the horizontal plane, facing anteriorly. In the illustrated example, at the general center of the meeting point of the interior faces 21 is an internal hole 23, which runs along an anterior-posterior axis. A portion of the internal hole 23 may include a threaded portion 26. Moreover, extending through the body of the posterior wedge 30 is an internal hole 33 which runs axially from posterior to anterior and is on the same axis as the internal hole 23 of the anterior wedge 20. A portion of the internal hole 33 may include an internal thread 34. For example, a posterior portion of the internal hole 33 may include an internal thread 34. In some examples, the anterior portion of the internal hole 33 may be smooth. In the depicted example, running parallel to the interior faces 21 and extending posteriorly from the anterior wedge body are guide tracks 24 on each lateral edge of the interior faces 21. In the illustrated example, a set of connector holes 25 are disposed on the guide tracks 24, which run along a lateral axis. Further in the depicted example, extending anteriorly on the lateral edges of the angled faces 31 of the posterior wedge 30 are a set of guide tabs 35. In the illustrated embodiment, a set of connector holes 36 are disposed on the guide tabs 35 which run along a lateral axis. As shown in the depicted example, the connector holes 36 may also intersect the internal hole 33.

In the illustrated embodiment, the endplates 40 each have an anterior interior face 41 and a posterior interior face 42. As shown in the exemplary embodiment, the interior faces 41 and 42 may be angled. For example, the anterior interior faces 41 may be approximately 45 degrees from the horizontal plane, facing anteriorly. Similarly, the posterior interior faces 42 may be approximately 45 degrees from the horizontal plane, facing posteriorly. The anterior interior faces 41 of the endplates 40 may rest against the interior faces 21 of the anterior wedge 20. Similarly, the posterior interior faces 42 may rest against the interior faces 31 of the posterior wedge 30.

In the depicted example, one or more elongated connector slots 43 extend laterally through the endplates 40. In some examples, each endplate 40 has at least one connector slot 43 disposed parallel to its anterior interior face 41 and at least one connector slot 43 disposed parallel to its posterior interior face 42. As shown in FIG. 11, in some examples, each endplate 40 may have two connector slots 43 disposed parallel to its anterior interior face 41 and two connector slots 43 disposed parallel to its posterior interior face 42. In the illustrated embodiment, the elongated connector slots 43 may define a movement boundary for the connectors 60. In some examples, the connectors 60 are in a first slot position when the implant 10 is in an unexpanded configuration (as shown in FIGS. 1, 3, 5, and 8), and a second slot position when the implant 10 is in an expanded configuration (as shown in FIGS. 2, 4, 6, 7, and 8). In some embodiments, the connector slots 43 may prevent the endplates 40 from over-extending, and the implant 10 from over-expanding.

In the illustrated example, the lateral edges of the anterior interior face 41 of each endplate 40 include a set, for example, a pair, of anterior guide grooves 44. Similarly, the lateral edges of the posterior interior face 42 of each endplate 40 include a set, for example, a pair of posterior guide grooves 45. In some scenarios, the anterior guide grooves 44 of the endplates 40 may ride against or along guide tracks 24 of the anterior wedge 20, in some cases, to prevent lateral movement of the endplate 40 with respect to the anterior wedge 20. Similarly, the posterior guide grooves 45 of the endplates 40 may be configured to ride against or along the guide tabs 35 of the posterior wedge 30, in some cases, to prevent the lateral movement of the endplates 40 with respect to the posterior wedge 30.

In the illustrated embodiment, the endplates 40 are radially displaced from the threaded post 50 longitudinal axis as a result of the anterior wedge 20 movement toward the posterior wedge 30, as the threaded post 50 was rotated, to expand the implant 10. In some embodiments, one or more connectors 60 connect the anterior end of the endplates 40 to the anterior wedge 20. In some embodiments, one or more connectors 60 also connect the posterior end of the endplates 40 to the posterior wedge 30. In some examples, connectors 60 prevent the implant from over-expanding. In the illustrated example, connector holes 25 and 36 disposed on the anterior and posterior wedges 20 and 30, respectively, are aligned with connector slots 43 disposed on the endplates 40 configured to retain connectors 60. In some examples, the connectors 60 are inserted through the connector slots 43 and into connector holes 25 and 36 to connect the endplates 40 to each of the anterior wedge 20 and the posterior wedge 30. In some embodiments, as the endplates 40 are radially displaced from the threaded post 50, the connectors 60 limit the expansion of the endplates 40. For example, the connectors may limit the vertical expansion of the endplates 40 by pivoting, sliding, or otherwise moving from a first predetermined position to a second predetermined position, while staying engaged with both the endplates 40 and the anterior and posterior wedges 20 and 30. In the depicted embodiment, the anterior portion of the endplates 41 maintains engagement with the anterior wedge 20 and the posterior portion of the endplates 40 maintains engagement with the posterior wedge 30. In some examples, the retention groove 54 of the threaded post 50 may prevent the threaded post 50 from inadvertently translating or moving within the posterior wedge 30, and in some scenarios, may prevent the posterior wedge 30 from moving with respect to the anterior wedge 20 when the threaded post 50 is rotated.

In the illustrated embodiment, an internal hole 33 in the posterior wedge 30 is configured to accept the threaded post 50, to permit the rotation of the threaded post 50 within the posterior wedge 30. In the depicted example, a locking screw 70 is utilized to lock the threaded post 50 in place and lock the implant 10 in an expanded position. In some examples, the locking screw 70 may have a drive feature 72 and may be inserted into the implant 10 by an inserter or driver having a corresponding drive feature. In accordance with some embodiments, the locking screw 70 may be configured to substantially abut the threaded post 50, to substantially lock the threaded post 50 in a desired location (e.g. at a desired expansion position of the implant 10) and prevent the threaded post 70 from unscrewing or dislodging.

In accordance with embodiments of the present invention, the endplates 40 may include ridges or teeth 46 configured to bite into bone and secure the implant 10 to the spine. In some embodiments, an exterior portion of the endplates 40 may include at least one recess configured to receive bone graft material. The endplates 40 and the bone graft material may be configured to maintain contact with a vertebral body once the implant 10 is implanted. In some examples, at least a portion of the bone graft material may be porous.

In accordance with an exemplary usage scenario, when the threaded post 50 is rotated, the threaded post 50 pulls the anterior wedge 20 posteriorly toward the posterior wedge 30, directing the endplates 40 to ride against the wedges, which drive the endplates 40 apart from one another, thereby increasing the height (e.g. the vertical distance) of the implant 10.

In some scenarios, a surgeon may insert the implant 10 into the spine of a patient, for example, between a pair of vertebrae. The surgeon may rotationally drive the threaded post 50 which axially couples the posterior wedge 30 to the anterior wedge 20 with an implant installation tool. In some examples, the anterior wedge 20 may move axially along the threaded post 50 toward the posterior wedge 30, as the surgeon turns the threaded post 50. In accordance with exemplary embodiments of the implant 10, each endplate 40 may be configured with a posterior interior face 42 slidably resting on the posterior wedge 30 and an anterior interior face 41 slidably resting on the anterior wedge 20. In some examples, the anterior wedge 20 may be directed posteriorly toward the posterior wedge 30 when a surgeon rotates the threaded post 50. In some scenarios, the action of directing the anterior wedge 20 toward the posterior wedge 30 directs the interior faces 41 and 42 of the endplates 40 to ride or slide against the interior faces 21 and 31 of the wedges 20 and 30, respectively. Moreover, the anterior guide grooves 44 of the endplates 40 may ride against or along guide tracks 24 of the anterior wedge 20, in some cases, to prevent lateral movement of the endplate 40 with respect to the anterior wedge 20. Similarly, the posterior guide grooves 45 of the endplates 40 may be configured to ride against or along the guide tabs 35 of the posterior wedge 30, in some cases, to prevent the lateral movement of the endplates 40 with respect to the posterior wedge 30. In some examples, the retention groove 54 of the threaded post 50 may prevent the threaded post 50 from inadvertently translating or moving within the posterior wedge 30, and in some scenarios, may prevent the posterior wedge 30 from moving with respect to the anterior wedge 20 when the threaded post 50 is rotated. The endplates 40, for example, a pair of opposing endplates 40, may be forced apart from one another by riding against the anterior and posterior wedges 20 and 30, thereby expanding the distance between the two endplates 40, and more generally, increasing the height of the implant 10. In some examples, the lateral rails 22 of the anterior wedge 20, which may ride within the lateral grooves 32 of the posterior wedge 30, may prevent any twisting of the anterior wedge 20, or the binding of the implant 10.

Although various embodiments have been described with reference to the Figures, other embodiments are possible. For example, various embodiment expandable interbody implant designs may include a posterior wedge and anterior wedge that are adapted to receive a threaded post axially between the two. Some embodiment implant implementations may also have two separate longitudinal moveable endplates. In an illustrative example, an implant implementation having two longitudinal moveable endplates aligned parallel to the threaded post. In some embodiments, each endplate may also have corresponding angled faces which mate to the angled faces of the wedges. In an exemplary usage scenario, as the threaded post turns, the threaded post draws the anterior and posterior wedges toward each other axially guided by the rails extending from the posterior wedge. In some examples, the rails extending from the anterior wedge engage with the posterior wedge rail inserts to prevent rotation of either or both of the anterior and posterior wedges. In some examples, the anterior wedge has an opening with an interior thread, corresponding to the threaded portion of the threaded post. In an illustrative example, rotating the threaded post draws the wedges toward each other pushes the wedges against the endplates. In some scenarios, the endplates are pushed outward vertically and expand the implant as the wedges are pushed against the endplates by the turning threaded post drawing the wedges toward each other. In some examples, the posterior wedge includes indentations which enable an inserter to act as counter-torque on the implant while the threaded post is turned.

In some examples, as the spinal implant expands, it does so with the implant endplates moving vertically and parallel to one another. The expansion of the endplates may be limited by the connectors connecting the endplates anteriorly to the anterior wedge and posteriorly to the posterior wedge. Thereby, the movement of the various components is limited during expansion which prevents the inadvertent disassembly of the implant. In some examples, the connector holes disposed on the anterior and posterior wedges, aligned with the anterior and posterior connector slots disposed on the endplates configured to retain connectors. In some examples, the connectors are inserted through the endplate slots and into wedge connector holes to connect the endplates to each of the anterior wedge and the posterior wedge. In some embodiments, as the endplates are radially displaced from the threaded post, the connectors limit the vertical expansion of the endplates. For example, the connectors may limit the vertical expansion of the endplates by pivoting, sliding, or otherwise moving from a first predetermined position in the connector slots to a second predetermined position in the connector slots while staying engaged with both the endplates and the anterior and posterior wedges. In some examples, the anterior portion of the endplates maintains engagement with the anterior wedge and the posterior portion of the endplates maintains engagement with the posterior wedge.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most fastener %" means fastener % or less than fastener %. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An implant configured to expand in at least one dimension, comprising:
   a first wedge having two or more angled faces and a pair of aligning rails, wherein each rail of the pair of aligning rails extends from opposite sides of the first wedge;
   a second wedge opposite the first wedge and formed with a pair of rail inserts that are configured to slidably receive the pair of aligning rails, wherein each rail insert of the pair of rail inserts are formed in opposite sides of the second wedge;
   a threaded post rotatably retained within the implant by holes formed in the first and second wedges;
   one or more endplates slidably engaged with the first wedge and the second wedge;
   two or more connectors operably connecting the first wedge to a first end of each endplate and the second wedge to the second end of each endplate; and
   wherein the threaded post is configured to rotate to draw the first wedge toward the second wedge thereby driving the endplates outward to expand the implant as the threaded post turns, and the connectors are configured to limit the vertical displacement of each of the endplates.

2. The implant of claim 1, wherein each of the endplates further comprise one or more interior angled faces configured slidably engage with one or more interior angled faces of the first wedge and the second wedge.

3. The implant of claim 1, the threaded post is formed with a retention groove configured to prevent the threaded post from translating within the second wedge.

4. The implant of claim 3, wherein the retention groove prevents the second wedge from moving relative to the first wedge when the threaded post is rotated.

5. An implant configured to expand in at least one dimension, comprising:

a first wedge having at least one angular wedge face vertically disposed in a first plane;

a second wedge having at least one angular wedge face vertically disposed in the first plane, wherein the second wedge is operably coupled to the first wedge by an aligning support;

a pair of movable endplates, each having a first end with one or more interior angled faces adapted to slidably engage with at least one first angular wedge face and a second end with one or more interior angled faces adapted to slidably engage with at least one second angular wedge face;

a threaded post formed with a retention groove, wherein the threaded post is longitudinally disposed between and operably connecting the first and second wedges and configured to rotate to draw the first wedge towards the second wedge and drive the endplates outward to expand the implant as the threaded post turns; and one or more connectors that connect the first end of each endplate to the first wedge and the second end of each endplate to the second wedge, wherein one or more of the one or more connectors pass through the retention groove formed in the threaded post.

6. The implant of claim 5, wherein the aligning support is a pair of rails laterally extending from the first wedge and configured to engage with rail inserts disposed on the second wedge.

7. The implant of claim 5, wherein the connectors are adapted to adjustably couple each of the of the endplates with each of the first wedge and the second wedge.

8. The implant of claim 5, wherein a locking member abuts the threaded post and is configured to prevent the threaded post from turning and the implant from disassembling.

9. The implant of claim 5, wherein the retention groove and the connectors passing through the retention groove are collectively configured to prevent the threaded post from translating within the second wedge.

10. An implant configured to expand in at least one dimension comprising:

a first base having a pair of angular faces meeting at a first edge to form an anterior wedge, a first internal hole formed on the first edge and having an internal threaded portion, and a pair of guide tracks having one or more anterior connector holes formed thereon, each guide track disposed on opposing sides of the first edge and extending toward an aligning support;

a second base having a pair of angular faces meeting at a second edge to form a posterior wedge, one or more guide tabs having one or more posterior connector holes, each guide tab disposed on opposing sides of the second edge, and a second internal hole formed on the second edge;

a threaded post having a first end with a threaded portion rotatably retained within the first internal hole and a second end formed with a retention groove and rotatably disposed within the second internal hole;

two movable endplates, each endplate comprising a first end with one or more anterior interior angled faces slidably engaged with at least one anterior wedge face and a second end with one or more posterior interior angled faces slidably engaged with at least one posterior wedge face, each end of the endplates having one or more endplate connector slots substantially aligned with the anterior and posterior connector holes;

four connectors, a first pair of connectors each disposed in the anterior wedge connector holes and the endplate connector slots to operably connect the first end of the endplates to the anterior wedge, and a second pair of connectors, each disposed in the posterior wedge connector holes and the endplate connector slots, and engaged with the threaded post retention groove;

wherein the rotation of the threaded post directs the first base towards the second base and slidably engages the interior faces of the endplates with the angular faces of the anterior and posterior wedges, to drive the endplates radially outward from the longitudinal axis of the threaded post, displacing the wedges and vertically expanding the implant; and, wherein the endplate connector slots define a movement boundary for the connectors and limit the displacement of each of the endplates.

11. The implant of claim 10, wherein the endplate connector slots are elongated.

12. The implant of claim 10, wherein an exterior portion of each of the endplates is includes a plurality of ridges or teeth.

13. The implant of claim 10, wherein a locking member abuts the threaded post and is configured to prevent the threaded post from turning.

14. The implant of claim 13, wherein the locking mechanism is a locking screw having an external threaded portion and a drive feature.

15. The implant of claim 10, the retention groove is configured to prevent the threaded post from translating within the second base.

16. The implant of claim 15, wherein the retention groove prevents the second base from moving relative to the first base when the threaded post is rotated.

17. The implant of claim 10, wherein the endplates slidably engage with one or more faces of the guide tracks and guide tabs of the first and second bases to prevent the lateral movement of the endplates with respect to the first base.

* * * * *